United States Patent
McCollum

(10) Patent No.: US 9,329,127 B2
(45) Date of Patent: May 3, 2016

(54) FLUORESCENCE SCANNING HEAD WITH MULTIBAND DETECTION

(75) Inventor: Tom McCollum, Berkeley, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 318 days.

(21) Appl. No.: 13/449,061

(22) Filed: Apr. 17, 2012

(65) Prior Publication Data

US 2013/0102481 A1 Apr. 25, 2013

Related U.S. Application Data

(60) Provisional application No. 61/480,144, filed on Apr. 28, 2011.

(51) Int. Cl.
- *C40B 60/12* (2006.01)
- *G01N 21/64* (2006.01)
- *G01N 21/25* (2006.01)
- *G01N 35/02* (2006.01)

(52) U.S. Cl.
CPC .......... *G01N 21/6428* (2013.01); *G01N 21/253* (2013.01); *G01N 21/6452* (2013.01); *G01N 35/028* (2013.01); *C40B 60/12* (2013.01); *G01N 2021/6419* (2013.01); *G01N 2021/6421* (2013.01); *G01N 2201/0627* (2013.01)

(58) Field of Classification Search
None
See application file for complete search history.

(56) References Cited

U.S. PATENT DOCUMENTS

| | | | |
|---|---|---|---|
| 5,173,808 A | 12/1992 | Auer et al. | |
| 6,236,456 B1 | 5/2001 | Giebeler et al. | |
| 6,614,525 B1 | 9/2003 | Engelhardt et al. | |
| 7,733,488 B1 | 6/2010 | Johnson | |
| 2002/0060791 A1* | 5/2002 | Stumbo et al. | 356/317 |
| 2004/0046956 A1 | 3/2004 | Gould et al. | |
| 2006/0177850 A1 | 8/2006 | Schermer et al. | |
| 2007/0121099 A1 | 5/2007 | Matsumoto et al. | |
| 2008/0030628 A1 | 2/2008 | Lundquist et al. | |
| 2008/0117425 A1 | 5/2008 | Kain | |
| 2008/0198448 A1 | 8/2008 | Ganser et al. | |
| 2009/0309049 A1 | 12/2009 | Van Dijk et al. | |
| 2010/0203572 A1 | 8/2010 | Lehmann et al. | |

FOREIGN PATENT DOCUMENTS

| | | |
|---|---|---|
| JP | 2008-139543 A | 6/2008 |
| JP | 2009-122203 A | 6/2009 |
| WO | 2006/061640 A2 | 6/2006 |
| WO | 2009/054870 A2 | 4/2009 |
| WO | 2010/088514 A1 | 8/2010 |
| WO | 2010/134104 A1 | 11/2010 |
| WO | 2012/035852 A1 | 7/2012 |

OTHER PUBLICATIONS

International Search Report and Written Opinion for PCT/US2012/035852, 11 pages, mailed Jul. 31, 2012.
The Extended European Search Report from EP Appl. 12776158.3 dated Oct. 10, 2014.
Office Action from JP Appl. 2014-508184, dated Oct. 6, 2014. *English translation version.*

* cited by examiner

*Primary Examiner* — Christian Boesen
(74) *Attorney, Agent, or Firm* — Kilpatrick Townsend & Stockton LLP

(57) ABSTRACT

In a scanning system for the detection and discrimination of a plurality of targets in each of a plurality of samples, one or more multiband fluorescence detection channels each of which contains a single multiband emission filter and a single detector replaces multiple detection components in scanning heads of the prior art. In certain embodiments, a single multi-emitter light source is used as well, to illuminate each sample with excitation light at a variety of distinct wavelengths in succession.

20 Claims, No Drawings

FLUORESCENCE SCANNING HEAD WITH MULTIBAND DETECTION

CROSS-REFERENCE TO RELATED APPLICATION

This application claims the benefit of U.S. Provisional Patent Application No. 61/480,144, filed Apr. 28, 2011, the contents of which are incorporated herein by reference in their entirety.

BACKGROUND OF THE INVENTION

1. Field of the Invention

This invention resides in the field of scanning systems for arrays of biological samples, particularly where each sample contains two or more targets that are individually labeled.

2. Description of the Prior Art

Detection systems that detect multiple species in each of a large number of samples or reaction mixtures are typified by the thermal cyclers that are used in performing the polymerase chain reaction (PCR). In PCR and other such systems, the samples or reaction mixtures are typically distributed among individual wells arranged in two-dimensional arrays, such as in a conventional microtiter plate, and monitoring of the sample conditions and the progress of each reaction requires separate detection and quantitation of each of the target species in each well. Such monitoring is commonly achieved by the attachment of fluorescent labels to the target species with a distinct label bound to each target, and detection and quantitation of the targets are achieved by optical scanning in which each label receives excitation light at a wavelength band appropriate to the label and the emission light resulting from each excited label is separately detected. Since the excitation bands of different fluorophores are often close together and frequently overlap, as do the emission bands, common scanning systems contain a separate optical system for each fluorophore and thus each target. A six-color system, for example, will contain six separate optical channels in the scanning head, each channel containing its own light source (typically a light-emitting diode, or LED), its own excitation filter, its own dichroic mirror, its own emission filter, its own set of lenses, and its own detector. The scanning head is then aligned with six wells at once, with a single optical channel aimed at each well, and the head is driven across the well array in one-well increments along both axes so that each well is ultimately exposed to all six optical systems. The number of course will vary with the number of targets, and hence the number of colors. In all cases, however, the scanning head suffers from a high part count, bulky construction, and high cost.

SUMMARY OF THE INVENTION

The limitations of conventional scanning systems as described above are addressed herein by a scanning head in which the multiple detection components are replaced with one or more multiband fluorescence detection channels, each of which contains a multiband emission filter and a detector. With this arrangement, the scanning head can be driven across the array of sample wells in the same manner as the scanning heads of the prior art, and the excitation light is received by, and the emission light is detected from, each well, with multiple fluorophores detected before moving to the next well. Scanning can thus be achieved by a simpler scanning motion with a smaller scanning head. In embodiments in which the scanning head contains two or more multiband detection channels, the different channels can either have identical multiband emission filters or different multiband emission filters. When two or more multiband emission filters are included that pass the same emission bands, the scanning heads can scan in parallel, each one scanning a portion of the wells in the planar array and thereby allowing scanning to occur in a fraction of the time that would be required for a single detection channel, i.e., two channels can scan the same expanse of wells in one-half the time, three channels in one-third the time, etc. When two or more multiband emission filters are included that pass different emission bands, the bands may be complementary with each other, i.e., collectively addressing all of the fluorescent labels in each well. Certain embodiments of the scanning head will however include a single multiband fluorescence detection channel with a single multiband emission filter and a single detector. In certain embodiments of the invention, the excitation light is supplied by a single multiband light source that produces light beams of different wavelength bands in succession, each wavelength band selected to excite one of the various target fluorophores. The single multiband light source is further combined in certain embodiments with a single multiband excitation filter to further ensure that the fluorophores are excited individually with minimal or no overlap in fluorophore excitation.

DETAILED DESCRIPTION OF THE INVENTION AND SPECIFIC EMBODIMENTS

Each multiband filter in the detection channels described herein can be a filter that not only passes emission light at selected wavelengths but also refines the passed emission light into discrete bands before the emission light reaches the detector. This refinement can narrow the width and sharpen the boundaries of each band, and can also provide broader separations between adjacent bands. In many cases, as certain examples below demonstrate, each multiband detection filter blocks the passage of light at the wavelengths used for excitation, a useful effect when excitation light is reflected off the sample and may otherwise reach the detector. All of these refinements allow the detection system to more clearly distinguish between emissions from different fluorophores to minimize false signals. Multiband filters suitable for use in the detection channel in the practice of the present invention are known in the art and commonly used in conjunction with fluorescence microscopes as well as protective eyewear. Among the known multiband filters are those that contain multiple layers applied over a substrate or otherwise laminated together, the layers differing in refractive index. Multiband filter sets can also be used, such as Forster Resonance Energy Transfer (FRET) filter sets. FRET filter sets, which are available from Horiba Instruments Inc., Ann Arbor, Mich., USA, and from Chroma Technology Corp., Bellows Falls, Vt., USA, are useful when matched pairs of fluorophores that exhibit energy transfer are used, i.e., where the emission from one fluorophore of the pair produces a secondary emission from the second fluorophore, and the secondary emission is used as the emission to be detected.

Multiband filters of all kinds are commercially available at a variety of wavelength bands and combinations of wavelength bands. In many cases, the bands have widths of 50 nm or less, and in many of these cases, the bands are from about 10 nm to about 30 nm in width. Separations between adjacent bands are often at least 20 nm, and in many cases the separations fall within the range of about 30 nm to about 75 nm. These values and ranges can vary. The number of bands generally will be at least as great as the number of distinct fluorescent labels used as labels for the target molecules. In most cases, the filter will transmit in at least three non-overlapping bands, and preferably from three to eight non-overlapping bands. While custom filters can be fabricated by methods known in the art, multiband filters that are presently available from commercial suppliers of such filters emit light in two, three or four bands.

As noted above, certain embodiments of this invention utilize a scanning head that includes only one multiband emission filter, while others utilize two or more multiband emission filters. In embodiments utilizing a single multiband emission filter and a single detector, a filter can be used that passes light emitted by all of the fluorescent labels contained in any single sample, thus allowing the scanning head to perform a complete set of detections of the labels with a single detection channel. In embodiments utilizing two or more multiband emission filters, each passing the same combination of wavelength bands but in separate fluorescence detection channels, and possibly a separate light source for each channel, a number of samples equal to the number of detection channels can be illuminated and detected simultaneously, thereby allowing a large array of samples to be detected in a relatively short period of time. In these embodiments, the different detection channels will move together, or will remain stationary as the sample array is moved, synchronously performing their functions in parallel. In embodiments utilizing two or more multiband emission filters, each passing a different combination of wavelength bands, the different combinations may overlap or duplicate certain bands, but they may also complement each other without duplication. Whether or not the different wavelength combinations include duplicative bands, the detection channels can be arranged such that all channels receive emission light from a single well at a time, or from separate wells, in which case the scanning protocol will be designed such that all emissions from each well will be detected. Multiple scanning heads can also be used, each with its own light source, multiband emission filter, and detector, each scanning a portion of the sample array and collectively covering all points in the array. In any embodiments utilizing multiple multiband emission filters, the number of such filters will generally be two to six, and in most cases two or three.

The detector can be any detector that converts impinging light to a measurable signal, i.e., a photodetector. Both imaging sensors and non-imaging sensors can be used. Examples of imaging sensors are CCDs and CMOSs. An examples of a non-imaging sensor is a photodiodes. Other examples are photoresistors, photomultiplier tubes, and certain LEDs. A photodetector that does not itself discriminate between different emission wavelengths can be used, as can photodetectors that emit different signals for different wavelengths.

The light source can be a single light source with selectivity among multiple wavelength bands, such as a multi-emitter LED or a multi-emitter semiconductor laser, or it can be a group of individual light sources emitting at different bands. When individual light sources are used, they can be oriented to provide off-axis illumination, i.e., with multiple sources distributed around the axis of a single well, each directing its beam at an angle toward the center of the well. As individual light sources, LEDs, lasers, fiber optics, and other conventional components can be used.

When a multi-emitter light source, i.e., one with multiple excitation bands integrated into a single light source, is used, a multiband excitation filter can be included to further shape the excitation bands that illuminate the sample wells, similar to the multiband emission filter. The use of such a refining filter in the excitation light pathway will provide each band with a more narrow bandwidth and sharper boundaries, as well as broader separations between adjacent excitation bands. These adjustments can be done to more closely match the illumination light to the individual fluorophores. The multiband filters for inclusion in the excitation light path are commercially available or obtainable, as are the multiband filters to be included in the detection channel, and all such filters can be made to specified bands by conventional manufacturing procedures well known in the art. The ranges for bandwidths and separations between adjacent bands for the multiband excitation filter are approximately the same as those cited above for the multiband emission filter.

While the particular colors (wavelength bands), wavelength bandwidths, and number of different colors can vary widely, one example of a multi-emitter LED that can serve as a light source is one emitting at three colors, red, green, and blue, respectively. As a fourth color, yellow is one example and violet is another. Still further examples and numbers of colors will be readily apparent to those skilled in the art. As one example of a three-color system, the excitation wavelength bands can be those having peaks at 485 nm, 555 nm, and 650 nm, while the emission bands can be centered at 515 nm, 600 nm, and 730 nm, respectively. In another example, the excitation wavelength bands are those having peaks at 473 nm, 545 nm, and 640 nm, while the emission bands can be centered at 498 nm, 576 nm, and 659 nm, respectively. In a third example, the excitation wavelength bands are those having peaks at 465 nm, 535 nm, and 617 nm, while the emission bands can be centered at 502 nm, 575 nm, and 675 nm, respectively. Still other examples will be readily apparent.

Particularly with a photodetector that does not itself discriminate between emission light from the various fluorophores in each sample, the discrimination between fluorophores can be achieved by correlating the timing of the emission signal with the timing of the excitation light pulse. Each emission signal will thus be associated with the excitation light pulse directed at a particular fluorophore, and the resulting signals can be sorted by a timing mechanism in the detection system. Each target species in any single sample can thus be detected, identified, and quantitated individually.

A beam splitter is commonly included in scanning systems to form different light paths for excitation and emission light, particularly when excitation is performed along the axis of the scan head and well. In scanning heads of the present invention, a dichroic beam splitter can be used in either of two orientations. In one orientation, the beam splitter is oriented to transmit excitation light, thereby allowing it to pass through the mirror, while reflecting emission light, that would otherwise travel back along the excitation light path, sideways to the detector. In another orientation, the light source is positioned to one side of the well axis while the detector is along the axis. The beam splitter in the latter case will be oriented to reflect the excitation light along the well axis and into the well while transmitting emission light to the detector. Other orientations will be readily apparent to those skilled in the art. With off-axis illumination, the beams are readily separated without a beam splitter. Useful beam splitters include 50:50 beam splitters, dichroic beam splitters, and multiband beam splitters. A 50:50 beam splitter does not split light into beams based on a difference in wavelength, but can be used in conjunction with the multiband filters to produce the desired wavelength discrimination. A dichroic beam splitter can be used to discriminate between excitation and emission wavelengths when the excitation wavelengths are either all below or all above the emission wavelengths. A multiband beam splitter can be matched to particular excitation and emission bands. A multiband beam splitter can thus be designed to efficiently reflect the light from the LEDs (when a multi-emitter LED is used) while providing high transmission of light at the fluorescent emission wavelength bands from the sample fluorophores.

In further variations, illumination and detection can both be performed from the open top of the sample well, i.e., by epi-illumination. With epi-illumination, scanning of the well array is most conveniently achieved by translational movement of the scanning head while the well array is held stationary. Trans-illumination, which illumination is directed underneath each well and through the well floor while detection is performed above, can also be used. With trans-illumination, scanning of the well array is best achieved by moving the array itself. With trans-illumination, scanning of the well array is most conveniently achieved by translational movement of the well array while the scanning head is held stationary.

The well array to be scanned by the scanning system of this invention can be a linear array or a two-dimensional array. The term "planar array" is used herein to include both linear and two-dimensional arrays. In either case, scanning can be achieved either by translational movement of the scanning head or of the array itself, or both. When scanning of a two-dimensional well array is achieved by translational motion of the scanning head, the scanning head can be moved across each row in succession, using alternating directions for adjacent rows. Translational motion can be achieved by conventional means, including conventional drive pulleys and motors, voice coil actuators, and the like. In one example, a voice-coil actuator is used to scan wells along the length of each row, and an electric motor and drive screw are used to advance the scanning head from one row to the next upon the completion of each row. Rotary motors, stepper motors, worm gears, and other conventional units can be used.

The various embodiments described above are of value in instrumentation for real-time PCR (polymerase chain reaction) as well as any application where multiple sites in a one- or two-dimensional array are to be illuminated for detection, and quantitation when desired, of two or more species at each site, particularly in multiplex analyses.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A scanning system for detection and discrimination of a plurality of targets in each of a plurality of samples, each target bearing a distinct fluorescent label, said scanning system comprising:
    a sample plate with a planar array of sample wells disposed therein;
    a scanning head comprising:
    (i) a light source actuatable to supply excitation light at a plurality of excitation wavelengths, each of said excitation wavelengths selected to excite one of said fluorescent labels;
    (ii) a plurality of multiband emission filters, each arranged to receive emission light emitted by two or more of said fluorescent labels upon excitation of said labels by said excitation light, and to pass said emission light so received in individually distinguishable wavelength bands, each said wavelength band including emission light from one of said fluorescent labels; and
    (iii) a separate detector for each said multiband emission filter, wherein the detector is a non-imaging sensor that converts light impinging thereon to a measurable signal, said detector arranged to receive emission light passing through said multiband emission filter; and
    drive motors or mechanisms for causing translational movement of said scanning head over each of said sample wells in succession,
    wherein different multiband emission filters pass light in different combinations of wavelength bands, the combinations do not duplicate wavelength bands, said plurality of said multiband emission filters collectively passes light emitted by all of said fluorescent labels.

2. The scanning system of claim 1 wherein said light source is actuatable to supply said excitation light at each of said plurality of excitation wavelengths in succession.

3. The scanning system of claim 1 wherein each of said multiband emission filters blocks passage of said excitation light.

4. The scanning system of claim 1 wherein each of said multiband emission filters blocks passage of said excitation light.

5. The scanning system of claim 1 wherein said light source is a single light source producing light at multiple wavelength bands with selectivity among said wavelength bands.

6. The scanning system of claim 5 wherein said light source is a multi-emitter LED.

7. The scanning system of claim 6 wherein said multi-emitter LED is a three-color LED.

8. The scanning system of claim 6 wherein said multi-emitter LED is a four-color LED.

9. The scanning system of claim 1 wherein said light source is a combination of individual light sources each emitting light at different wavelength bands, one said band including excitation light for each of said fluorophores.

10. The scanning system of claim 1 wherein said non-imaging sensor is a photodiode.

11. The scanning system of claim 1 wherein said wavelength bands passed by said multiband emission filter are from about 10 nm to about 30 nm in width, with adjacent said bands separated by from about 30 nm to about 75 nm.

12. A process for monitoring reactions between a plurality of species in each of a plurality of samples arranged in a planar array, each species bearing a distinct fluorescent label, said process comprising scanning said planar array with a scanning head in accordance with claim 1 to illuminate each of said species in each of said samples with excitation light at excitation wavelengths for the fluorescent labels borne by said species and to detect emission light emitted by each of said fluorescent labels.

13. The process of claim 12 comprising scanning said planar array by translational movement of said scanning head relative to said planar array while maintaining said planar array stationary.

14. The process of claim 12 comprising scanning said planar array by translational movement of said planar array relative to said scanning head while maintaining said scanning head stationary.

15. The process of claim 12 wherein said planar array is a linear array.

16. The process of claim 12 wherein said planar array is a two-dimensional array.

17. The process of claim 12 wherein said light source is actuatable to emit said excitation light at each of said plurality of excitation wavelengths in succession, and said process comprises illuminating each sample with successive illuminations of excitation light at each of said plurality of excitation wavelengths.

18. The scanning system of claim 1, wherein the scanning head further comprises a dichroic beam splitter configured to form different light paths for excitation and emission light, wherein the dichroic beam splitter is oriented to transmit excitation light and reflect emission light.

19. The scanning system of claim 1, wherein the scanning head further comprises a 50:50 beam splitter.

20. The scanning system of claim 1, wherein each detector does not itself discriminate between different emission wavelengths.

* * * * *